United States Patent
Yokota et al.

(10) Patent No.: US 8,614,349 B2
(45) Date of Patent: Dec. 24, 2013

(54) OXIDATION CATALYST AND OXIDATION METHOD

(75) Inventors: Koshiro Yokota, Tokyo (JP); Tatsuo Yamaguchi, Tokyo (JP); Toru Watanabe, Tokyo (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 874 days.

(21) Appl. No.: 11/666,240

(22) PCT Filed: Nov. 17, 2005

(86) PCT No.: PCT/JP2005/021123
§ 371 (c)(1),
(2), (4) Date: Apr. 25, 2007

(87) PCT Pub. No.: WO2006/054643
PCT Pub. Date: May 26, 2006

(65) Prior Publication Data
US 2008/0091044 A1    Apr. 17, 2008

(30) Foreign Application Priority Data

Nov. 17, 2004 (JP) .............................. P2004-333411

(51) Int. Cl.
*C07C 67/00* (2006.01)
*C07C 69/02* (2006.01)

(52) U.S. Cl.
USPC ........................................ 560/241; 560/231

(58) Field of Classification Search
None
See application file for complete search history.

(56) References Cited

U.S. PATENT DOCUMENTS

| | | | |
|---|---|---|---|
| 6,552,220 B1* | 4/2003 | Obana et al. | 562/538 |
| 6,911,563 B2* | 6/2005 | Mizukami et al. | 568/802 |
| 2003/0078453 A1* | 4/2003 | Springer et al. | 562/534 |
| 2004/0110995 A1 | 6/2004 | Mizukami et al. | |

FOREIGN PATENT DOCUMENTS

| | | |
|---|---|---|
| EP | 1361206 | 11/2003 |
| JP | 5-4935 A | 1/1993 |
| JP | 5-163179 A | 6/1993 |
| JP | 5-245373 A | 9/1993 |
| JP | 5-294859 A | 11/1993 |
| JP | 2002-205968 A | 7/2002 |
| JP | 2002-540942 A | 12/2002 |
| WO | WO-00/61535 A1 | 10/2000 |

OTHER PUBLICATIONS

Vilcu R. et al. Journal of Thermal Analysis, vol. 41 (1994) 1335-1341.*
Kantarci, N, Process Biochemistry 40 (2005) 2263-2283.*
John McMurry, *Organic Chemistry*, 3rd Edition, 1992, Brooks/Cole Publishing Co. pp. 804 and 817.
Supplemental European Search Report in European application No. 05807059.0 dated Nov. 25, 2009.

* cited by examiner

*Primary Examiner* — Clinton Brooks
(74) *Attorney, Agent, or Firm* — Birch, Stewart, Kolasch & Birch, LLP

(57) ABSTRACT

The present invention provides a method for oxidizing a hydrocarbon, an alcohol or an aldehyde, which comprises: oxidizing a hydrocarbon, an alcohol or an aldehyde to an alcohol, an aldehyde, a carboxylic acid or a carboxylate ester corresponding thereto, in a liquid phase having: a region in which oxygen is substantially present; and a region in which oxygen is substantially absent, in the presence of a catalyst containing a palladium, wherein the region in which oxygen is substantially absent is 0.1 to 10% by volume with respect to a total of the region in which oxygen is substantially present and the region in which oxygen is substantially absent.

6 Claims, No Drawings

OXIDATION CATALYST AND OXIDATION METHOD

FIELD OF THE INVENTION

The present invention relates to a method for oxidizing a hydrocarbon, an alcohol or an aldehyde to an alcohol, an aldehyde, a carboxylic acid, or a carboxylate ester corresponding thereto in a liquid phase in the presence of a catalyst containing a palladium.

BACKGROUND ART

In general, in a liquid-phase oxidation reaction, a dissolution of a catalyst component often becomes a problem. This is a phenomenon in which the catalyst component is dissolved out, and which may be considered a problem inherent to the liquid-phase oxidation reaction. For solving such problem, there is adopted a method of combining a base metal with a precious metal constituting the principal catalyst component and causing such base metal to be dissolved out, as in a palladium-copper catalyst often employed in a Wacker type oxidation reaction (Reference 1 or 2), palladium-heteropoly acid employed in a synthesis of acetic acid by an ethylene process (Reference 3), or palladium-tellurium employed in a synthesis of glyceric acid (Reference 4), namely sacrificing the base metal thereby suppressing the dissolution of the precious metal.

The dissolution of the catalyst component, being triggered by an oxidation of the catalyst component, may be suppressed by reducing a concentration or a partial pressure of oxygen, but such method will retard the oxidation reaction which is an intended main reaction. Consequently the method of sacrificing the base metal has been often employed as an unavoidable method, and a solution for such situation has been desired.

[Reference 1] JP 5-163179 A
[Reference 2] JP 5-294859 A
[Reference 3] JP 2002-540942 A
[Reference 4] JP 5-245373 A

DISCLOSURE OF THE INVENTION

Problems to be Resolved by the Invention

The present invention is to provide, in a liquid-phase oxidation reaction for oxidizing a hydrocarbon, an alcohol, or an aldehyde to an alcohol, an aldehyde, a carboxylic acid or a carboxylate ester corresponding thereto with oxygen in the presence of a catalyst, an oxidation method capable of employing a same reaction condition for from less easily oxidized hydrocarbons to easily oxidized aldehyde, with an ordinary agitated tank reactor and with a relatively mild reaction condition, to realize a high yield in alcohol, aldehyde, carboxylic acid or carboxylate ester, and also capable of effectively suppressing the dissolution of the catalyst component, which is a problem in the liquid-phase oxidation reaction.

Means of Solving the Problems

As a result of intensive studies undertaken by the present inventors so as to solve the aforementioned problems, it is found that the reaction system does not simply require the presence of oxygen but requires a region where the oxygen is substantially absent, and the starting point of the present invention has thus been reached.

Since the present invention relates to an oxidation reaction, an idea of forming a region in which oxygen is substantially absent means forming a region where the reaction does not proceed. Thus the idea was thought contrary to the common knowledge of those skilled in the art. It has been, however, totally unexpectedly found that the formation of the region in which oxygen is substantially absent makes it possible to maintain a high reactivity.

Formation of a region in which oxygen is substantially absent has been found, not only providing such advantage of maintaining a high reactivity, to effectively suppress the dissolution of the catalyst component constituting a problem in the liquid-phase oxidation reaction, and the present invention has thus been made.

Also it is found that the effect of suppressing the dissolution of the catalyst component can be further enhanced by the presence of palladium bonded with hydrogen (Pd—H) on the catalyst, and a further extension of the present invention has thus been attained. The present inventors estimate that a stabilization of the catalyst component takes place thereby enabling to execute a reaction of obtaining an alcohol, an aldehyde, a carboxylic acid or a carboxylate ester with a high yield over a prolonged period.

More specifically, the present invention relates to those of following items 1 to 6.

1. A method for oxidizing a hydrocarbon, an alcohol or an aldehyde, which comprises: oxidizing a hydrocarbon, an alcohol or an aldehyde to an alcohol, an aldehyde, a carboxylic acid or a carboxylate ester corresponding thereto, in a liquid phase having: a region in which oxygen is substantially present; and a region in which oxygen is substantially absent, in the presence of a catalyst containing a palladium, wherein the region in which oxygen is substantially absent is 0.1 to 10% by volume with respect to a total of the region in which oxygen is substantially present and the region in which oxygen is substantially absent.

2. The method for oxidizing a hydrocarbon, an alcohol or an aldehyde according to item 1, wherein a catalyst in the region in which oxygen is substantially absent has Pd—H.

3. The method for oxidizing a hydrocarbon, an alcohol or an aldehyde according to item 1 or 2, wherein the oxidation method is a method for producing an alcohol and/or a carboxylic acid from a hydrocarbon.

4. The method for oxidizing a hydrocarbon, an alcohol or an aldehyde according to item 1 or 2, wherein the oxidation method is a method for producing a carboxylic acid and a carboxylate ester from an alcohol and/or an aldehyde.

5. A method for producing a carboxylic acid, which comprises hydrolyzing a carboxylate ester obtained by a method according to item 4.

6. A method for producing a carboxylate ester, which comprises esterifying a carboxylic acid obtained by a method according to item 3 or 4.

Advantageous Effects of the Invention

The present invention allows, in a liquid-phase oxidation reaction for oxidizing a hydrocarbon, an alcohol, or an aldehyde to an alcohol, an aldehyde, a carboxylic acid or a carboxylate ester corresponding thereto with oxygen in the presence of a catalyst, to employ a same reaction condition for from less easily oxidized hydrocarbons to easily oxidized aldehyde, in an ordinary agitated tank reactor and with a relatively mild temperature condition, to realize a high yield in alcohol, aldehyde, carboxylic acid or carboxylate ester, and also to effectively suppress the dissolution of the catalyst component, which is a problem in the liquid-phase oxidation reaction, and is therefore highly useful.

BEST MODE FOR CARRYING OUT THE INVENTION

In the following, the present invention will be explained in detail.

A feature of the present invention resides in an oxidation method in which oxidization is carried out in a liquid phase having a region in which oxygen is substantially absent, which is provided in a specified proportion with respect to a total of a region where a region in which oxygen is substantially present and the region in which oxygen is substantially absent.

The region in which oxygen is substantially absent has an upper limit, in % by volume (hereinafter referred to as vol. %), of 10%, preferably 5% and more preferably 3%, and a lower limit of 0.1%, preferably 0.2% and more preferably 0.3% with respect to a total of a region where a region in which oxygen is substantially present and the region in which oxygen is substantially absent. The region in which oxygen is substantially absent is preferably 0.1 to 10 vol. % with respect to a total of the region in which oxygen is substantially present and the region in which oxygen is substantially absent In case the region in which oxygen is substantially absent exceeds 10 vol. %, the main oxidation reaction may be undesirably hindered. Also in case the region in which oxygen is substantially absent is less than 0.1 vol. %, the effect of suppressing the dissolution of the catalyst component may become undesirably insufficient.

Although it is feared, in the presence of such region in which oxygen is substantially absent, that the main oxidation reaction is hindered, in the present invention, a loss in the yield of the oxidation reaction is in fact not observed in the presence of such region in which oxygen is substantially absent.

In the present invention, a region in which oxygen is substantially present means a region where molecular oxygen is present together with a supported palladium catalyst and a raw material (hydrocarbon, alcohol or aldehyde), and the molecular oxygen may be present in a gaseous state or in a dissolved state in the raw material liquid with a high concentration close to a saturated solubility.

In the present invention, a region in which oxygen is substantially absent means a region where molecular oxygen is absent in the vicinity of the catalyst including a palladium. The molecular oxygen does not exist at least in the gaseous state, and, even in case it is dissolved in a region where the catalyst and the reaction liquid alone are mixed, such dissolved oxygen is preferably in a state consumed by the reaction. An amount of the dissolved oxygen in the region in which oxygen is substantially absent is preferably one-half of the saturated concentration of the dissolved oxygen, more preferably one-third thereof, still more preferably one-quarter thereof. The saturated concentration of the dissolved oxygen varies based on a kind of used solvent, temperature, pressure and gas phase oxygen concentration. For example, under a condition of 80° C., 5 kg/cm$^2$-G, gas phase oxygen concentration of 8%, in methanol, the saturated concentration of the dissolved oxygen is about 50 ppm. The saturated concentration of the dissolved oxygen can be measured by using a concentration meter such as MC-7GS manufactured by Iijima Electronics Corp.

A reactor type capable of realizing a reaction system of the present invention can be a bubble column reactor or an agitated tank reactor having a sedimentation tank (which includes one having a downcomer) in which the catalyst is suspended in the raw material liquid and a oxygen-containing gas is blown into, a trickle bed reactor in which the catalyst is fixed in the reactor, while the raw material liquid flows in a discontinuous phase and a oxygen-containing gas flows in a continuous phase, or a cage type agitated tank reactor in which the catalyst is fixed by a cage or the like in the agitated tank and the reaction liquid alone flows. Also there can be advantageously employed a loop type reactor including two reactors, one of which is supplied with an oxygen-containing gas while the other is supplied with an oxygen-free gas, and which mutually supply the reaction liquid containing the catalyst.

For example, when using the bubble column reactor or an agitated tank reactor having a sedimentation tank in which the catalyst is suspended in the raw material liquid and a oxygen-containing gas is blown into, in the decanter, the gaseous oxygen is absent and the dissolved oxygen is also consumed in the reaction, whereby the oxygen is substantially absent in the vicinity of the catalyst. Accordingly, the whole of the reaction liquid existing in the sedimentation tank is the region in which oxygen is substantially absent in this case. Same applies to a case that the reactor has the downcomer.

When using the trickle bed reactor, a method that a gas containing oxygen and a gas that does not contain oxygen such as nitrogen, carbon dioxide or inert gas is flowed alternately into a region having a reacting solution and a catalyst including a palladium. For example, the region in which oxygen is substantially absent is controlled to 5 vol. % by flowing a gas having oxygen for 10 minutes and an inert gas for 30 seconds alternately.

When using the cage type agitated tank reactor, the region in which oxygen is substantially absent can be provided and controlled in a same way as the case of using the trickle bed reactor.

When using a loop type reactor, it is possible to flow an oxygen-containing gas in one reactor thereby causing the main reaction to proceed and to flow an inert gas such as nitrogen in the other reactor thereby forming a region in which oxygen is substantially absent.

The hydrocarbon to be employed in the present invention can be selected from very wide compounds, for example an aliphatic saturated lower hydrocarbon such as methane, ethane, propane or butane, an aliphatic higher saturated hydrocarbon such as decane, tridecane or tetradecane, an aliphatic lower unsaturated hydrocarbon such as ethylene, propylene or 1-butene, an aliphatic higher unsaturated hydrocarbon such as 1-decene, 1-dodecene or 1-tetradecene, an aromatic hydrocarbon such as benzene, toluene or xylene, a condensed polycyclic aromatic hydrocarbon such as anthracene or naphthalene, and a combined compound of such aliphatic hydrocarbon and aromatic hydrocarbon. Such hydrocarbons may be employed singly or as a mixture of arbitrary two or more kinds.

Among these, ethylene, propylene, 1-butene, benzene, toluene or xylene is employed preferably.

The alcohol to be employed in the present invention can be an aliphatic saturated alcohol such as methanol, ethanol, isopropanol or octanol; a diol such as ethylene glycol or butanediol; an aliphatic unsaturated alcohol such as allyl alcohol or methallyl alcohol; or an aromatic alcohol such as benzyl alcohol. In particular, methanol or ethanol is preferred because of a fast reaction. Such alcohols may be employed singly or in a mixture of arbitrary two or more kinds. There is also preferred an alcohol formed by oxidation of a hydrocarbon.

The aldehyde to be employed in the invention is an aliphatic saturated aldehyde, an aliphatic unsaturated aldehyde, an aromatic aldehyde or a derivative thereof, and examples include an aliphatic saturated aldehyde such as formaldehyde, acetaldehyde, propionaldehyde, isobutyl aldehyde, or glyoxal; an aliphatic unsaturated aldehyde such as acrolein, methacrolein, or crotonaldehyde; an aromatic aldehyde such as benzaldehyde, tolylaldehyde, benzyl aldehyde or phthalaldehyde; and an aldehyde derivative such as dimethyl acetal or diethyl acetal of the aforementioned aldehydes. Such aldehyde may be employed singly or in a mixture of arbitrary two or more kinds. There is also preferred an aldehyde formed by oxidation of a hydrocarbon or an alcohol. In particular, acrolein or methacrolein can be employed preferably.

In the present invention, "corresponding" means that an oxidation merely takes place without changing a number of carbon atoms. For example in case of employing ethylene as the reaction substrate, a corresponding alcohol is ethanol, a corresponding aldehyde is acetaldehyde, a corresponding carboxylic acid is acetic acid, and a corresponding carboxylate ester is acetic ester.

In the present invention, various compounds with significantly different reactivity are oxidized with a same catalyst and under a same reaction condition, but an obtained product is variable depending on the reaction substrate.

For example, a hydrocarbon such as propylene or benzene employed in the present invention provides various products such as an alcohol, an aldehyde, and a carboxylic acid, but the aldehyde is often oxidized to carboxylic acid because of its high reactivity, so that an alcohol and carboxylic acid are principally obtained as product.

The present oxidation method provides a carboxylic acid and a carboxylate ester, and a desired carboxylic acid can be obtained by hydrolyzing the obtained carboxylate ester, and a desired carboxylate ester can be obtained by esterifying the obtained carboxylic acid.

In the present invention, a hydrocarbon, an alcohol and an aldehyde may be employed singly or in a mixture thereof.

In case of executing a reaction of an aldehyde and an alcohol in the present invention, a ratio of aldehyde and alcohol is not particularly restricted and may be selected within a wide range such as an aldehyde/alcohol molar ratio of 10 to 1/1000, but a lower amount of aldehyde is generally preferable, and a molar ratio within a range of 1/2 to 1/50 is preferred.

The catalyst to be employed in the present invention is a catalyst containing a palladium.

The catalyst to be employed in the present invention has to contain palladium. Also a catalyst containing palladium and X (X being at least a metal selected from lead, bismuth, mercury and thallium) is employed preferably, and palladium and X may form an alloy or an intermetallic compound.

It may further contain a different element such as Fe, Te, Ni, Cr, Co, Cd, In, Ta, Cu, Zn, Zr, Hf, W, Mn, As, Ag, Re, Sb, Sn, Rh, Ru, Ir, Pt, Au, Ti, Al, B, Si, Ge, Se or Ta. Such different element may be preferably contained in an amount of 5 wt. % or less, and more preferably 1 wt. % or less with respect to the amount of the carrier in general.

Also a catalyst containing at least one selected from an alkali metal compound and an alkali earth metal compound provides an advantage of increasing the reactivity. The alkali metal or alkali earth metal is preferably contained within a range of 0.01 to 30 wt. % and preferably 0.01 to 5 wt. % with respect to the amount of the carrier in general.

Such different element, or a compound of alkali metal or alkali earth metal may intrude by a small amount in the crystal lattice, or may substitute a part of the metal of the crystal lattice. Also the compound of alkali metal and/or alkali earth metal may be added, at the catalyst preparation, to a solution containing a palladium compound or an X compound, thereby being adsorbed or deposited on a carrier, or a carrier carrying such substance in advance may be used for the catalyst preparation. Also such compound may be added to the reaction system under the reacting condition.

Such catalyst-constituting component is preferably carried singly on a carrier such as silica, alumina, silica-alumina, titanium, a carbonate salt, a hydroxide, active charcoal, or zirconia.

In the present invention, when a catalyst containing a palladium is a palladium-supported catalyst, in which a palladium is supported on a carrier, a loaded amount of the palladium-supported catalyst is not particularly restricted, but is preferably in a range of 0.1 to 20 wt. %, more preferably 1 to 10 wt. % in general with respect to the amount of the carrier. In case of employing an alkali metal compound or an alkali earth metal compound as a carrier, a loaded amount of the palladium is preferably in a range of 0.01 to 30 wt. % and more preferably 0.01 to 15 wt. % in general with respect to the amount of the carrier.

The catalyst of the invention can be prepared by a known preparing method. In case of a catalyst is only a palladium, a commercially available palladium/active charcoal catalyst can be employed conveniently. In case of a catalyst containing palladium and X (X being at least a metal selected from lead, bismuth, mercury and thallium), a representative preparation method is to add a carrier in an aqueous solution containing a soluble lead compound and a soluble palladium salt such as palladium chloride, thereby impregnating lead and palladium under heating, and then to execute a reduction with formalin, formic acid, hydrazine or hydrogen gas. In this example, lead may be carried before palladium is carried, or palladium and lead may be carried simultaneously.

The palladium compound to be employed for catalyst preparation can be suitably selected from an organic acid salt such as a formate salt or an acetate salt; an inorganic acid salt such as a sulfate salt, a hydrochlorate salt or a nitrate salt; an organometallic complex such as an ammine complex, a benzonitrile complex, an acetylacetonate-complex or a carbonyl complex; an oxide and a hydroxide, but is preferably palladium chloride or palladium acetate.

Compounds of X (X being at least a metal selected from lead, bismuth, mercury and thallium) can be an inorganic salt such as a nitrate salt or an acetate salt, or an organometallic complex such as a phosphine complex, and is preferably a nitrate salt or an acetate salt.

Also when using a catalyst including the alkali metal compound or the alkali earth metal compound, the alkali metal compound or the alkali earth metal compound is preferably selected from an organic acid salt, an inorganic acid salt and a hydroxide.

An amount of the catalyst can be varied within a wide range depending on a type of reaction raw material, a composition or a preparation method of the catalyst, conditions and type of reaction, and, in case of a reaction in a slurry state, the catalyst is preferably employed in an amount of 0.04 to 0.5 kg in 1 liter of the reaction liquid.

In the present invention, the reaction system is preferably maintained at pH 6 to 9 by further adding a compound of an alkali metal or an alkali earth metal (such as an oxide, a hydroxide, a carbonate salt or a carboxylic acid salt) to the reaction system. In particular, a pH value of 6 or higher provides an effect of preventing dissolution of the component X (X being at least a metal selected from lead, bismuth, mercury and thallium) in the catalyst. Such compound of an alkali metal or an alkali earth metal may be employed singly or in a combination of two or more kinds. The amount of a compound of an alkali metal or an alkali earth metal can be controlled so as to obtain the target value of pH based on a temperature of the reaction system, a kind of acid, a concentration of acid and a concentration of water.

The present invention can be executed at a high temperature of 100° C. or more, but the oxidation method of the present invention is preferably executed at 30 to 100° C. and more preferably 60 to 90° C. A reaction time is not particularly restricted, and cannot be defined uniquely as it is variable depending on the selected conditions, but is generally 1 to 20 hours.

The present invention can provide an even better effect by the presence of Pd—H defined in the following steps a to d:

a. After the reaction, the catalyst is stored in a condition not contacting oxygen or a compound having an active hydrogen, and is separated under nitrogen at the room temperature. The operation is conducted in a dry box which is often utilized for handling an organometallic complex and which is constantly subjected to elimination of oxygen and moisture;

b. There is prepared a temperature programmed desorption apparatus capable of heating a measuring cell from room temperature to 450° C. by 100° C./h and sucking and analyzing liberated gas by a gas chromatography and a mass spectrometer, and the catalyst after the reaction is charged in the measuring cell;

c. A hydrogen amount in the liberated gas is measured. A mass spectrometer is preferably employed as it can trace the liberating behavior of hydrogen with a mass number 2 (a number obtained by dividing a mass m of a molecule or an atom to be measure by a number e of valence electrons, hereinafter represented as m/e) without a perturbation by other organic substances;

d. After the hydrogen liberation, the number of moles of the liberated hydrogen is determined. The liberated hydrogen means a total number of moles of hydrogen liberated from the sampled catalyst in the above-described measuring method, in the course of temperature increase in the temperature programmed desorption apparatus. The number of hydrogen atom is provided by doubling the number of moles that is obtained above, and the value of Pd—H (mol. %) is provided by dividing the number of hydrogen atom by the number of atoms of the target palladium. For example, when 100 μmol of palladium is included in a sampled catalyst, and the number of liberated hydrogen is determined as 1 μmol (2 μmol as hydrogen atom) by the thermal desorption apparatus, it is found that the sampling catalyst includes 2 μmol of Pd—H, and the value of Pd—H is calculated as 2 mol %.

In the present invention, the palladium catalyst preferably contain thus quantified Pd—H. Aproportion Pd—H to Pd in the catalyst is preferably 10 mol. % or less, more preferably 3 mol. % or less and further preferably 1 mol. % or less. Also a proportion Pd—H to Pd in the catalyst is preferably 0.001 mol. % or higher, more preferably 0.003 mol. % or higher and further preferably 0.01 mol. % or higher.

Example 1

The present invention is now illustrated in greater detail with reference to Examples and Comparative Examples, but it should be understood that the present invention is not to be construed as being limited thereto.

(1) Handling of Catalyst in the Present Invention

A dry box employing for handling organometallic complexes was prepared, and the catalyst was handled therein. Nitrogen supplied in the dry box was supplied from a liquid nitrogen container, and nitrogen passed through an oxygen-eliminating column such as a large-sized Oxygen Trap (trade name of a deoxygen tube of GL Science Inc.) and a moisture-eliminating column filled with calcium hydride or phosphor pentoxide was circulated to constantly execute oxygen elimination and moisture elimination.

While it is a common knowledge in handling an organometallic compound that it tends to be electrostatically charged under dry nitrogen, it is also necessary to execute a demagnetizing operation in the dry box, as palladium shows paramagnetism. Furthermore, a grounding operation is also necessary.

The Pd—H was measured with a temperature programmed desorption apparatus MULTITASK-T.P.D., manufactured by Nippon Bell Co., by heating the measuring cell from the room temperature to 450° C. at a rate of 100° C./h and measuring the liberated gas of m/e=2 as hydrogen with a mass spectrometer.

(2) Example of Catalyst Preparation a. As a catalyst of palladium alone, a 5 wt. % palladium/active charcoal catalyst was prepared by a method described by Kunugi et al. (Kogyo-Kagaku Kaishi, 71, 1517 (1968)).

b. As a catalyst containing palladium and lead, a catalyst carrying palladium by 5 wt. %, lead by 5 wt. % and magnesium by 4 wt. % on a silica gel carrier (trade name: Carriact 10, average particle size: 50 μm) manufactured by Fuji Silicia Co., was prepared.

(3) Analysis of Reaction Results

A reaction liquid and a gas from the reactor exit were analyzed by an ordinary gas chromatography, utilizing GC-8A and GC-14BT, manufactured by Shimadzu Corp., mounted with a G-100 column manufactured by Chemicals Inspection and Testing Institute, Japan or a glass column filled with Gaschropack 56 manufactured by GL Science Inc., and also utilizing a flame ionization detector (FID) or a thermal conductivity detector (TCD) under a programmed control of a thermostat tank.

(4) Analysis of Catalyst Component in Reaction Liquid

An atomic absorption analysis of the reaction liquid was conducted with a atomic absorption analysis apparatus A-Analyst-100 manufactured by PerkinElmer Japan Co., Ltd., and by combusting the reaction liquid, without any pre-treatment, by an acetylene-oxygen flame burner. A calibration line was obtained by preparing a reference liquid of a similar composition from a standard sample.

When the reaction liquid is subjected to the induced plasma mass analysis, an ICP analysis of the reaction liquid was conducted by exacting weighing about 10 ml of the reaction liquid, and ashing it by gradually heating from the room temperature to about 600° C. in the air. The remaining ash was dissolved in aqua regia of a predetermined amount, and analyzed with ICPM-8500 manufactured by Shimadzu Corp. A calibration line was obtained by preparing a similar composition from a standard sample.

Example 1

In a 60-ml stainless steel autoclave equipped with a magnetic induction agitator having a sedimentation tank, 4.0 g of the catalyst described in (2)-a and 30 ml/h of methanol as a raw material were charged continuously, and a reaction was conducted under temperature of 50° C., a pressure of 7 kg/cm$^2$, a revolution of 1000 rpm (agitating chip speed: 1.2 m/s), and air and nitrogen was supplied so as to obtain an exit oxygen concentration of 6%. The amount of the reaction liquid in the reaction tank including the decanter was 30 ml, and the amount of the reaction liquid in the sedimentation tank was 3 ml, and then the region in which oxygen is substantially absent was 10 vol. %. The reaction result after 50 hours from the start of the reaction was that the yield of formic acid was 1.2%, and the yield of methyl formate was 78.9%.

The palladium concentration in the reaction liquid was measured as 0.2 ppm.

In this Example, the amount of Pd—H in the region in which oxygen is substantially absent was 3.0 mol. %.

Example 2

The reaction was carried out in the same manner as in Example 1, except that methanol was changed to methanol containing benzene by 5 mol. %. The reaction result after 50 hours from the start of the reaction was that the yield of phenol is 15%, the yield of formic acid was 1.0%, the yield of methyl formate was 73.8%.

The palladium concentration in the reaction liquid was measured as 0.2 ppm.

In this Example, the amount of Pd—H in the region in which oxygen is substantially absent was 2.8 mol. %.

Comparative Example 1

The reaction was carried out in the same manner as in Example 2, except that an agitated tank applying a filter separation method, in which a sintered stainless steel filter was placed in the agitated tank and the reaction liquid alone was extracted by a pressure difference, was used instead of the sedimentation method. In this case, the region in which the oxygen is substantially absent did not exist. The reaction result after 50 hours from the start of the reaction was that the yield of phenol is 15%, the yield of formic acid was 1.1%, and the yield of methyl formate was 73.2%.

The palladium concentration in the reaction liquid was measured as 0.7 ppm.

Example 3

The reaction was carried out in the same manner as in Example 2, except that benzene was changed to toluene. The reaction result after 52 hours from the start of the reaction was that the yield of formic acid was 0.9%, the yield of methyl formate was 71.2%, the yield of benzoic acid was 12%, the yield of methyl benzoate was 0.2%, the yield of the ester of formic acid and benzyl alcohol was 1%. In this example, benzyl alcohol was not detected.

The palladium concentration in the reaction liquid was measured as 0.2 ppm.

In this Example, the amount of Pd—H in the region in which oxygen is substantially absent was 2.7 mol. %.

Example 4

The reaction was carried out in the same manner as in Example 1, except that the alcohol was changed to ethanol and a reaction temperature of 80° C. was employed. The reaction result after 50 hours from the start of the reaction was that the yield of acetic acid was 4.4%, and the yield of ethyl acetate was 75.5%.

The palladium concentration in the reaction liquid was measured as 0.3 ppm.

In this Example, the amount of Pd—H in the region in which oxygen is substantially absent was 1.8 mol. %.

Example 5

10 g of the reaction liquid obtained by an overflow from the reactor in Example 4 was added with 100 g of distilled water, and then the mixture was hydrolyzed for 1 hour at 65° C. by employing AMBERLIST-15 (trade name of strongly acidic ion exchange resin, manufacture by Rohm and Haas Ltd.) by 5 wt. % as a catalyst so as to hydrolyze acetic ether to acetic acid. The yield of acetic acid based on ethanol was calculated as 75%.

Comparative Example 2

The reaction was carried out in the same manner as in Example 4, except that an agitated tank applying a filter separation method, in which a sintered stainless steel filter was placed in the agitated tank and the reaction liquid alone was extracted by a pressure difference, was used instead of the decantation method. In this case, the region in which oxygen is substantially absent did not exist. The reaction result after 50 hours from the start of the reaction was that the yield of acetic acid was 4.1%, and the yield of ethyl acetate was 74.8%.

The palladium concentration in the reaction liquid was measured as 1 ppm.

Example 6

150 g of a catalyst described in (2)-b were charged in an external circulation bubble column type stainless steel reactor having a downcomer and having a liquid phase capacity of 1.2 liters, and a reaction was conducted under supplies of methacrolein (34 wt. %)/methanol at a rate of 0.54 L/h and NaOH/methanol at a rate of 0.06 L/h, with a temperature of 80° C., a pressure of 5.03 kg/cm$^2$, and an air and nitrogen was supplied so as to obtain a reactor exit oxygen concentration of 4%. The concentration of NaOH was so regulated as to obtain pH 7.1 in the reaction liquid, and lead acetate was dissolved in methacrolein/methanol and continuously supplied so as to obtain a lead concentration of 20 ppm in the reaction liquid. The amount of the reaction liquid in the reaction tank including the sedimentation tank was 1.2 L, and the amount of the reaction liquid in the decanter was 30 ml, and then the region in which oxygen is substantially absent was 2.4 vol. %.

The reaction result after 500 hours from the start of the reaction was that the yield of methyl methacrylate was 55.5%, and the yield of methacrylic acid was 3.2%.

The palladium concentration in the reaction liquid was lower than 10 ppb in this case, which was the lower detection limit of the measuring apparatus. The lead concentration in the reaction liquid was 21 ppm, which was substantially same as the supplied concentration, and no apparent dissolution of the catalyst component was observed.

In this Example, the amount of Pd—H in the region in which oxygen is substantially absent was 0.1 mol. %.

Example 7

10 g of the reaction liquid obtained by an overflow from the reactor in Example 6 was hydrolyzed as same as Example 5 so as to hydrolyze methyl methacrylate to methacrylic acid. The yield of methacrylic acid based on methacrolein was calculated as 57%.

Comparative Example 3

The reaction was carried out in the same manner as in Example 6, except that an agitated tank applying a filter separation method, in which a sintered stainless steel filter was placed in the agitated tank and the reaction liquid alone was extracted by a pressure difference, was used instead of the decantation method. Since the volume of the liquid phase portion of the sintered filter portion was about 1 ml, the region in which oxygen is substantially absent was about 0.8 vol. %. The reaction was unstable, and the yields of methyl methacrylate and methacrylic acid were both gradually decreased.

The concentration of palladium in the reaction liquid was 0.1 ppm, and that of lead is 38 ppm.

Example 8

150 g of a catalyst described in (2)-b were charged in an external circulation bubble column type stainless steel reactor having a liquid phase capacity of 1.2 liters, and a reaction was conducted by supplying methacrolein (34 wt. %)/methanol at a rate of 0.54 L/h and NaOH/methanol at a rate of 0.06 L/h, with a temperature of 80° C., a pressure of 5.03 kg/cm$^2$, and air and nitrogen were supplied so as to obtain a reactor exit oxygen concentration of 4%. The concentration of NaOH was so regulated as to obtain, pH 7.1 in the reaction liquid, and lead acetate was dissolved, in methacrolein/methanol and continuously supplied so as to obtain a lead concentration of 2 ppm in the reaction liquid.

A slurry containing the catalyst and the reaction liquid was extracted by overflowing from the bubble column reactor A, and was transferred by a down-flow to a bubble column reactor B of a capacity of 120 ml, from which a slurry containing the catalyst and the reaction liquid was extracted by overflowing and was transferred by a down-flow to the bubble column reactor A.

Since an inert gas was actively flowed in the bubble column reactor B, the whole of the bubble column reactor B was the region in which oxygen is substantially absent, and the region in which oxygen is substantially absent is 9 vol. %.

The reaction liquid was extracted by a pressure difference from the top of the bubble column B utilizing a sintered stainless steel filter.

The yield of methyl methacrylate after 200 hours from the start of the reaction was 54.5% and that of methacrylic acid was 3.5%.

The palladium concentration in the reaction liquid was lower than 10 ppb, which was the lower detection limit of the measuring apparatus. The lead concentration in the reaction liquid was 2 ppm, which was substantially same as the supplied concentration, and no apparent dissolution of the catalyst component was observed.

The amount of Pd—H in the region in which oxygen is substantially absent was 0.4 mol. %.

Example 9

10 g of the reaction liquid obtained by an overflow from the reactor in Example 8 was hydrolyzed as same as Example 5 so as to hydrolyze methyl methacrylate to methacrylic acid. The yield of methacrylic acid based on methacrolein was calculated as 56%.

Comparative Example 4

The reaction was carried out in the same manner as in Example 8, except that the volume of the bubble column reactor B was 200 ml.

The reaction was unstable, and the yields of methyl methacrylate and methacrylic acid were both gradually decreased.

The palladium concentration and the lead concentration in the reaction liquid were lower than 10 ppb, which was the lower detection limit of the measuring apparatus, and no apparent dissolution of the catalyst component was observed.

The present invention allows, in a liquid-phase oxidation reaction for oxidizing a hydrocarbon, an alcohol, or an aldehyde to an alcohol, an aldehyde, a carboxylic acid or a carboxylate ester corresponding thereto with oxygen in the presence of a catalyst, to employ a same reaction condition for from less easily oxidized hydrocarbons to easily oxidized aldehyde, in an ordinary agitated tank reactor and with a relatively mild temperature condition close to the room temperature, to realize a high yield in alcohol, aldehyde, carboxylic acid or carboxylate ester, and also to effectively suppress the dissolution of the catalyst component, which is a problem in the liquid-phase oxidation reaction, and is therefore highly useful.

While the present invention has been described in detail and with reference to specific embodiments thereof, it will be apparent to one skilled in the art that various changes and modifications can be made therein without departing from the spirit and scope thereof.

The present application is based on Japanese Patent Application No. 2004-333411 filed on Nov. 17, 2004, and the contents thereof are incorporated herein by reference.

INDUSTRIAL APPLICABILITY

The present invention allows, in a liquid-phase oxidation reaction for oxidizing a hydrocarbon, an alcohol, or an aldehyde to an alcohol, an aldehyde, a carboxylic acid or a carboxylate ester corresponding thereto with oxygen in the presence of a catalyst, to employ a same reaction condition for from less easily oxidized hydrocarbons to easily oxidized aldehyde, in an ordinary agitated tank reactor and with a relatively mild temperature condition around a room temperature with using an inexpensive air, to realize a high yield in alcohol, aldehyde, carboxylic acid or carboxylate ester, and also to effectively suppress the dissolution of the catalyst component, which is a problem in the liquid-phase oxidation reaction, and is therefore highly useful.

The invention claimed is:

1. A method for oxidizing a hydrocarbon, an alcohol or an aldehyde, the method comprising:
    oxidizing a hydrocarbon, an alcohol or an aldehyde to an alcohol, an aldehyde, a carboxylic acid or a carboxylate ester corresponding thereto,
    in a liquid phase having:
       a region where oxygen being substantially present; and
       a region where oxygen being substantially absent,
    in the presence of a catalyst containing a palladium,
    the region where oxygen being substantially absent being 0.1 to 10% by volume with respect to a total of the region where oxygen being substantially present and the region where oxygen being substantially absent.

2. The method for oxidizing a hydrocarbon, an alcohol or an aldehyde according to claim 1,
    wherein a catalyst in the region in which oxygen is substantially absent has Pd—H.

3. The method for oxidizing a hydrocarbon, an alcohol or an aldehyde according to claim 1 or 2,
    wherein the oxidation method is a method for producing an alcohol and/or a carboxylic acid from a hydrocarbon.

4. The method for oxidizing a hydrocarbon, an alcohol or an aldehyde according to claim 1 or 2,
    wherein the oxidation method is a method for producing a carboxylic acid and a carboxylate ester from an alcohol and/or an aldehyde.

5. A method for producing a carboxylic acid, the method comprising hydrolyzing a carboxylate ester obtained by a method according to claim 4.

6. A method for producing a carboxylate ester, the method comprising esterifying a carboxylic acid obtained by a method according to claim 3.

* * * * *